(12) United States Patent
Daigo et al.

(10) Patent No.: US 7,458,995 B1
(45) Date of Patent: Dec. 2, 2008

(54) HAIR DYE COMPOSITIONS

(75) Inventors: Hiroyasu Daigo, Sayama (JP); Akimasa Mochizuki, Saitama (JP)

(73) Assignee: Arimino Co., Ltd. (JP)

( * ) Notice: Subject to any disclaimer, the term of this patent is extended or adjusted under 35 U.S.C. 154(b) by 210 days.

(21) Appl. No.: 11/629,434

(22) PCT Filed: Jun. 10, 2005

(86) PCT No.: PCT/JP2005/010718

§ 371 (c)(1),
(2), (4) Date: Dec. 13, 2006

(87) PCT Pub. No.: WO2005/120446

PCT Pub. Date: Dec. 22, 2005

(30) Foreign Application Priority Data

Jun. 14, 2004 (JP) ............................. 2004-176219

(51) Int. Cl.
*A61Q 5/10* (2006.01)
(52) U.S. Cl. .................. 8/405; 8/406; 8/408; 8/410; 8/411; 8/412; 8/421; 8/424; 8/435
(58) Field of Classification Search ............... 8/405, 8/408, 410, 411, 412, 421, 424, 435
See application file for complete search history.

(56) References Cited

U.S. PATENT DOCUMENTS

| | | | |
|---|---|---|---|
| 6,099,591 A | 8/2000 | Matravers et al. | |
| 6,139,853 A | 10/2000 | Akram et al. | |
| 6,383,232 B1 | 5/2002 | Wohlman et al. | |
| 6,565,615 B1 * | 5/2003 | Wong et al. | ..................... 8/408 |

FOREIGN PATENT DOCUMENTS

| | | |
|---|---|---|
| DE | 4445282 A1 | 6/1996 |
| JP | 2043722 B2 | 12/1981 |
| JP | 7173039 A | 7/1995 |
| JP | 2000297019 A | 10/2000 |

OTHER PUBLICATIONS

Journal of Technical Disclosure, No. 95-15922, "Hair Dye", Japan Institute of Invention and Innovation (9 pp.), English translation (18 pp.), no date.
Japanese Standards of Quasi-Drug Ingredients, Jun. 1991, Yakuji Nippo, Ltd. (6 pp), English translation of Table 3 (2 pp.).
Robbins, Clarence R., Chemical and Physical Behavior of Human Hair, Colgate-Palmolive Co., 6. Dyeing Human Hair, Apr. 15, 1982, pp. 119-140 with English translation (8 pp.).
Kato, Kazuo, Progress and Assignment of Permanent Hair Colorants, Fragrance Journal, Jun. 15, 1991, vol. 19, No. 6, pp. 30-35 with English translation (12 pp.).

* cited by examiner

*Primary Examiner*—Eisa B Elhilo
(74) *Attorney, Agent, or Firm*—The Webb Law Firm, P.C.

(57) ABSTRACT

A first hair coloring agent composition is a hair coloring agent composition comprising (A) one or more compounds selected from the group consisting of p-phenylenediamine, toluene-2,5-diamine and their salts, (B) α-naphthol and (C) resorcin (with the proviso that p-aminophenol is not contained), wherein the components (A) to (C) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, and the component (C) is contained in an amount of 0.45 to 1.5 parts by weight. A second hair coloring agent composition is a hair coloring agent composition further comprising (D) p-aminophenol in addition to the components (A) to (C), wherein the components (A) to (D) are contained in given amounts and in given weight ratios. The disclosed hair coloring agent compositions enable hair coloring which exhibit slow color fading and long-lasting color in which there is minimal change of hue in the hair even after color fading occurs.

12 Claims, No Drawings

HAIR DYE COMPOSITIONS

FIELD OF THE INVENTION

The present invention relates to a hair coloring agent composition, and more particularly to a hair coloring agent composition which hardly causes change of hue, brings about slow fading of a color and provides a long-lasting color even if hair washing is repeated after the hair coloring agent composition penetrates into hairs and develops a color.

BACKGROUND OF THE INVENTION

In recent years, a demand for hair coloring has increased, and the market of hair coloring has been extended more and more, as is called a "hair coloring boom".

Depending upon the types of dye components used, however, the colored hair has a problem that change of hue (discoloration) occurs because a part of dye compounds having undergone oxidation polymerization inside hairs are washed away in a biased ratio by hair washing and a problem that lightness of the hair tends to increase and the color is not long-lasting (color fading is liable to occur) because dye compounds having undergone oxidation polymerization inside hairs are washed away from hairs in a relatively short period of time. Problems of such discoloration and color fading are conspicuous especially when hair is colored a color tone having a medium or higher lightness (e.g., brown).

In connection therewith, in a patent document 1, an oxidation color development type black coloring agent containing, as active ingredients, 4,4'-diaminodiphenylamine, 1-naphthol, resorcin and m-aminophenol in given amounts is disclosed, and with regard to hair having been colored with the black coloring agent, color fastness to sunlight, potash soap and sweat has been studied. In the patent document 1, however, discoloration and color fading in other cases than the case where white or gray hair is colored black have not been studied, and also the color fastness having been studied is desired to be secured over a longer period of time.

In a patent document 2, a hair coloring agent composition comprising (a) one or more components selected from p-phenylenediamine, toluene-2,5-diamine and the like, (b) o-chloro-p-phenylenediamine or a water-soluble salt thereof and (c) α-naphthol is disclosed, and it is described that resorcin, m-aminophenol and o-aminophenol may be contained as arbitrary components. However, specifically disclosed as an embodiment containing α-naphthol is a hair coloring agent composition comprising 2,5,6-triamino-4-hydroxypyrimidine sulfate and α-naphthol or comprising these components and o-chloro-p-phenylenediamine sulfate, and with regard to a hair bunch having been colored with the composition, fastness to light is evaluated, but change of hue (discoloration) and color fading due to hair washing are not mentioned at all.

In a non-patent document 1, there is disclosed a hair coloring agent composition containing (a) one or more dye intermediates selected from p-phenylenediamine, toluene-2,5-diamine, 4,4'-diaminodiphenylamine, p-aminophenol, o-chloro-p-phenylenediamine and the like in an amount of 0.01 to 10% by weight and (b) one or more couplers selected from resorcin, α-naphthol and the like in an amount of 0.01 to 10% by weight, wherein the weight ratio of the dye intermediate (a):the coupler (b) is in the range of 1:10 to 10:1. In the non-patent document 1, however, color fastness (resistance to change in color and color fading) of the hair coloring agent composition is not studied at all.

Accordingly, there has been eagerly desired development of a hair coloring agent composition which hardly causes change of hue, brings about slow fading of a color and provides a long-lasting color even if hair washing is repeated after the hair coloring agent composition penetrates into hairs and develops a color.

Patent document 1: Japanese Patent Publication No. 43722/1990

Patent document 2: Japanese Patent Laid-Open Publication No. 173039/1995

Non-patent document 1: Journal of Technical Disclosure No. 15922/1995 issued by the Japan Institute of Invention and Innovation

SUMMARY OF THE INVENTION

It is an object of the present invention to provide a hair coloring agent composition which hardly causes change of hue, brings about slow fading of a color and provides a long-lasting color even if hair washing is repeated after the hair coloring agent composition penetrates into hairs and develops a color.

A first hair coloring agent composition according to the present invention is a hair coloring agent composition comprising (A) one or more compounds selected from the group consisting of p-phenylenediamine, toluene-2,5-diamine and their salts, (B) α-naphthol and (C) resorcin (with the proviso that p-aminophenol is not contained), wherein:

the components (A), (B) and (C) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, and the component (C) is contained in an amount of 0.45 to 1.5 parts by weight.

In the first hair coloring agent composition, it is preferable that at least p-phenylenediamine and/or its salt is contained as the component (A), and it is more preferable that p-phenylenediamine and/or its salt and toluene-2,5-diamine and/or its salt are contained as the component (A) in a molar ratio (p-phenylenediamine and/or its salt:toluene-2,5-diamine and/or its salt) of 0.226:1 to 5.65:1.

In the present invention, the components (A), (B) and (C) are preferably contained in a total amount of 0.1 to 5.0% by weight in the whole amount of the first hair coloring agent composition.

A second hair coloring agent composition according to the present invention is a hair coloring agent composition comprising (A) one or more compounds selected from the group consisting of p-phenylenediamine, toluene-2,5-diamine and their salts, (B) α-naphthol, (C) resorcin and (D) p-aminophenol, wherein:

the components (A), (B), (C) and (D) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, the component (C) is contained in an amount of 0.45 to 1.5 parts by weight, and the component (D) is contained in an amount of 0.05 to 2 parts by weight.

In the second hair coloring agent composition, it is preferable that at least p-phenylenediamine and/or its salt is contained as the component (A), and it is more preferable that p-phenylenediamine and/or its salt and toluene-2,5-diamine and/or its salt are contained as the component (A) in a molar ratio (p-phenylenediamine and/or its salt:toluene-2,5-diamine and/or its salt) of 0.226:1 to 5.65:1.

In the present invention, the components (A), (B), (C) and (D) are preferably contained in a total amount of 0.1 to 5.0% by weight in the whole amount of the second hair coloring agent composition.

According to the hair coloring agent composition of the invention, hair coloring which is almost free from change of hue, exhibits slow fading of a color and provides a long-lasting color is possible, and besides, even if color fading occurs, hue of hair is hardly changed. Therefore, the hair coloring agent composition is favorably used also for coloring faded hair a color of the same type again.

Accordingly, the hair coloring agent composition of the invention is advantageous particularly when hair is colored a color tone having a medium or higher lightness (e.g., brown), said color tone suffering conspicuous discoloration or color fading.

Further, the hair coloring agent composition of the invention has another advantage. That is to say, even in the case where coloring of hair having a virgin hair portion (uncolored hair portion) and an already-colored hair portion is carried out, these portions can be colored on the same level with the same agent without separately coloring these portions with different agents if a color difference between the virgin hair portion (uncolored hair portion) and the already-colored hair portion is relatively small.

DETAILED DESCRIPTION OF THE INVENTION

Hair Coloring Agent Composition

The first hair coloring agent composition according to the invention is a hair coloring agent composition comprising (A) one or more compounds selected from the group consisting of p-phenylenediamine, toluene-2,5-diamine and their salts, (B) α-naphthol and (C) resorcin (with the proviso that p-aminophenol is not contained), wherein:

the components (A), (B) and (C) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, and the component (C) is contained in an amount of 0.45 to 1.5 parts by weight.

In this specification, the term "dye component" has a meaning including both of an oxidation dye component and a direct dye (dye that develops a color even if it is not oxidized). In this specification, further, the term "oxidation dye component" has a meaning including both of a dye intermediate that develops a color when it is oxidized by an oxidizing agent (dye that develops a color when it is coupled with another oxidation dye or develops a color when it is used singly) and a so-called coupler that develops a color when it is used in combination with the dye intermediate.

Therefore, the components (A), (B) and (C) and the later-described component (D) all belong to the oxidation dye components.

Examples of the components (A) for use in the first hair coloring agent composition, that is, one or more compounds selected from the group consisting of p-phenylenediamine, toluene-2,5-diamine and their salts, include p-phenylenediamine, toluene-2,5-diamine, p-phenylenediamine sulfate, toluene-2,5-diamine sulfate, p-phenylenediamine hydrochloride and toluene-2,5-diamine hydrochloride. These compounds may be used singly or in combination of two or more kinds.

Of these, at least p-phenylenediamine and/or its salt is preferably used, and p-phenylenediamine and/or its salt and toluene-2,5-diamine and/or its salt are more preferably used in combination.

In the case where p-phenylenediamine and/or its salt and toluene-2,5-diamine and/or its salt are used in combination as the component (A), it is preferable to use them so that p-phenylenediamine and/or its salt and toluene-2,5-diamine and/or its salt should be contained in a molar ratio (p-phenylenediamine and/or its salt:toluene-2,5-diamine and/or its salt) of 0.226:1 to 5.65:1, and it is more preferable to use them so that p-phenylenediamine and/or its salt and toluene-2,5-diamine and/or its salt should be contained in a molar ratio (p-phenylenediamine and/or its salt:toluene-2,5-diamine and/or its salt) of 0.565:1 to 2.26:1. When p-phenylenediamine and/or its salt and toluene-2,5-diamine and/or its salt are used in combination in the above molar ratio, lasting of a color of the colored hair is further improved, whereby a progress of color fading can be inhibited.

In the case where p-phenylenediamine or its salt is used singly, the number of moles of the p-phenylenediamine and/or its salt to determine the molar ratio is a number of moles of each component, and in the case where p-phenylenediamine and its salt are used in combination, the number of moles of the p-phenylenediamine and/or its salt to determine the molar ratio is a total number of moles of those components.

Likewise, in the case where toluene-2,5-diamine or its salt is used singly, the number of moles of the toluene-2,5-diamine and/or its salt to determine the molar ratio is a number of moles of each component, and in the case where toluene-2,5-diamine and its salt are used in combination, the number of moles of the toluene-2,5-diamine and/or its salt to determine the molar ratio is a total number of moles of those components.

In the first hair coloring agent composition of the invention, (B) α-naphthol and (C) resorcin are contained together with the component (A), but p-aminophenol is not contained.

The α-naphthol (B) and the resorcin (C) are each a so-called coupler which hardly develops a color if it is oxidized alone but develops a color when it is oxidized together with a dye intermediate. By using these components (B) and (C) together with the component (A) in such a manner that they are contained in a given proportion (% by weight) to the total amount of dye components contained in the first hair coloring agent composition and contained in a given weight ratio based on the component (A), there can be obtained a first hair coloring agent composition which hardly causes change of hue and brings about slow fading of a color even if hair washing is repeated after the composition penetrates into hairs and develops a color.

More specifically, in the first hair coloring agent composition of the invention, the component (A), the α-naphthol (B) and the resorcin (C) are contained in a total amount of usually 60 to 100% by weight, preferably 75 to 100% by weight, more preferably 90 to 100% by weight, when the total amount of dye components in the hair coloring agent composition is 100% by weight, and based on 1 part by weight of the component (A), usually, the component (B) is contained in an amount of 0.1 to 1 part by weight and the component (C) is contained in an amount of 0.45 to 1.5 parts by weight, and preferably, the component (B) is contained in an amount of 0.25 to 1 part by weight and the component (C) is contained in an amount of 0.45 to 1.5 parts by weight, and more preferably, the component (B) is contained in an amount of 0.3 to 0.7 part by weight and the component (C) is contained in an amount of 0.5 to 1.2 parts by weight.

When the total amount (% by weight) of the components (A) to (C) occupied in the total amount of dye components contained in the hair coloring agent composition is in the above range and when the component (B) and the component (C) are each contained in the hair coloring agent composition in the above weight ratio based on the component (A), the hair colored with the hair coloring agent composition comprising the above components hardly suffers change of hue and undergoes color fading slowly by the interaction between these components, even if hair washing is repeated.

In the first hair coloring agent composition of the invention, the component (A), the α-naphthol (B) and the resorcin (C) are contained in a total amount of usually 0.1 to 5.0% by weight, preferably 0.5 to 3.0% by weight, in the whole amount of the hair coloring agent composition.

By the use of the hair coloring agent composition wherein the oxidation dye components having the aforesaid given weight ratios are contained in the aforesaid total amount, the following advantages are exhibited. For example, if hair is colored a color tone having a medium or higher lightness and even if the hair that is a target of coloring includes a virgin hair portion (uncolored hair portion), an already-colored hair portion and a white or gray hair, these portions can be colored fast, and besides, even if hair washing is repeated, change of hue (discoloration) and color fading hardly occur and the hair color is long-lasting.

The second hair coloring agent composition according to the invention is a hair coloring agent composition comprising (A) one or more compounds selected from the group consisting of p-phenylenediamine, toluene-2,5-diamine and their salts, (B) α-naphthol, (C) resorcin and (D) p-aminophenol, wherein:

the components (A), (B), (C) and (D) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, the component (C) is contained in an amount of 0.45 to 1.5 parts by weight, and the component (D) is contained in an amount of 0.05 to 2 parts by weight.

The second hair coloring agent composition is an embodiment wherein (D) p-aminophenol is further added in addition to the components of the first hair coloring agent composition. According to the studies by the present inventors, it has been ascertained that by using the p-aminophenol (D) together with the components (A) to (C) in such a manner that the components (A) to (D) are contained in a given proportion (% by weight) to the total amount of dye components contained in the second hair coloring agent composition and contained in a given weight ratio based on the component (A), change of hue (discoloration) and color fading of hair can be more effectively inhibited even if hair washing is repeated after coloring of hair.

Examples of the oxidation dye components (A) to (C) for use in the second hair coloring agent composition include the same ones as previously described for the oxidation dye components (A) to (C) for use in the first hair coloring agent composition. As the oxidation dye component (A), at least p-phenylenediamine and/or its salt is preferably used, and p-phenylenediamine and/or its salt and toluene-2,5-diamine and/or its salt are more preferably used in combination.

In the case where p-phenylenediamine and/or its salt and toluene-2,5-diamine and/or its salt are used in combination as the component (A), it is preferable to use them so that p-phenylenediamine and/or its salt and toluene-2,5-diamine and/or its salt should be contained in a molar ratio (p-phenylenediamine and/or its salt:toluene-2,5-diamine and/or its salt) of 0.226:1 to 5.65:1, and it is more preferable to use them so that p-phenylenediamine and/or its salt and toluene-2,5-diamine and/or its salt should be contained in a molar ratio (p-phenylenediamine and/or its salt:toluene-2,5-diamine and/or its salt) of 0.565:1 to 2.26:1. When p-phenylenediamine and/or its salt and toluene-2,5-diamine and/or its salt are used in combination in the above molar ratio, lasting of a color of the colored hair is further improved, whereby a progress of color fading can be inhibited.

When p-phenylenediamine or its salt is used singly, the number of moles of the p-phenylenediamine and/or its salt to determine the molar ratio is a number of moles of each component, and when p-phenylenediamine and its salt are used in combination, the number of moles of the p-phenylenediamine and/or its salt to determine the molar ratio is a total number of moles of those components.

Likewise, when toluene-2,5-diamine or its salt is used singly, the number of moles of the toluene-2,5-diamine and/or its salt to determine the molar ratio is a number of moles of each component, and when toluene-2,5-diamine and its salt are used in combination, the number of moles of the toluene-2,5-diamine and/or its salt to determine the molar ratio is a total number of moles of those components.

In the second hair coloring agent composition of the invention, the component (A), the α-naphthol (B), the resorcin (C) and the p-aminophenol (D) are contained in a total amount of usually 60 to 100% by weight, preferably 75 to 100% by weight, more preferably 90 to 100% by weight, when the total amount of dye components in the hair coloring agent composition is 100% by weight, and based on 1 part by weight of the component (A), usually, the component (B) is contained in an amount of 0.1 to 1 part by weight, the component (C) is contained in an amount of 0.45 to 1.5 parts by weight, and the component (D) is contained in an amount of 0.05 to 2 parts by weight, and preferably, the component (B) is contained in an amount of 0.25 to 1 part by weight, the component (C) is contained in an amount of 0.45 to 1.5 parts by weight, and the component (D) is contained in an amount of 0.1 to 1.5 parts by weight, and more preferably, the component (B) is contained in an amount of 0.3 to 0.7 part by weight, the component (C) is contained in an amount of 0.5 to 1.2 parts by weight, and the component (D) is contained in an amount of 0.2 to 1 part by weight.

When the total amount (% by weight) of the components (A) to (D) occupied in the total amount of dye components contained in the hair coloring agent composition is in the above range and when the components (B) to (D) are each contained in the hair coloring agent composition in the above weight ratio based on the component (A), the hair colored with the hair coloring agent composition comprising the above components hardly suffers change of hue (discoloration) and undergoes color fading slowly by the interaction between these components, even if hair washing is repeated. In particular, the second hair coloring agent composition contains the component (D), and hence, the effect of inhibiting discoloration and color fading is more improved.

In the second hair coloring agent composition of the invention, the component (A), the α-naphthol (B), the resorcin (C) and the p-aminophenol (D) are contained in a total amount of usually 0.1 to 5.0% by weight, preferably 0.5 to 3.0% by weight, in the whole amount of the hair coloring agent composition.

By the use of the hair coloring agent composition wherein the oxidation dye components having the aforesaid given weight ratios are contained in the aforesaid total amount, the following advantages are exhibited. For example, if hair is colored a color tone having a medium or higher lightness and even if the hair that is a target of coloring includes a virgin hair portion (uncolored hair portion), an already-colored hair portion and a white or gray hair, these portions can be colored fast, and besides, even if hair washing is repeated, change of hue (discoloration) and color fading hardly occur and the hair color is long-lasting.

Both of the first hair coloring agent composition and the second hair coloring agent composition of the invention preferably further contain an alkali component. The amount of the alkali component contained in the hair coloring agent composition is desired to be an amount corresponding to a case where 28 wt % aqueous ammonia is contained in an amount of usually 0.1 to 20% by weight, preferably 1 to 15% by weight, more preferably 3 to 10% by weight, in the whole amount (100% by weight) of the hair coloring agent composition.

Although the alkali component is not specifically restricted, examples thereof include aqueous ammonia, monoethanolamine, diethanolamine, triethanolamine, morpholine, ammonium carbonate, ammonium hydrogencarbonate, sodium carbonate, sodium hydrogencarbonate, guanidine hydrogencarbonate, sodium hydroxide, potassium hydroxide, arginine, monoisopropanolamine and 2-amino-2-methylpropanol. These alkali components can be used singly or in appropriate combination. When the first hair coloring agent composition and the second hair coloring agent composition of the invention contain an alkali component other than aqueous ammonia, the amount of the alkali component in the hair coloring agent composition can be determined in the following manner. The amount of the alkali component is measured by neutralization titration using 0.1N hydrochloric acid and then compared with a calibration curve of an amount of an alkali component obtained by separate measurement using a composition containing, as an alkali component, aqueous ammonia only.

The first hair coloring agent composition and the second hair coloring agent composition of the invention usually further contain water in addition to the aforesaid components. As water, purified water such as ion-exchanged water or distilled water is preferably employed. The water content is not specifically restricted and has only to be such an amount that the components used for the hair coloring agent composition can be sufficiently dissolved or dispersed.

The pH of the first hair coloring agent composition and the second hair coloring agent composition of the invention is in the range of usually 5.0 to 11.5, preferably 8.0 to 11.0.

If desired, to the first hair coloring agent composition and the second hair coloring agent composition of the invention may be appropriately added publicly known components which can be generally added to a hair coloring agent composition in amounts not detrimental to the object of the present invention, in addition to the aforesaid components.

Examples of other components which can be added include other oxidation dyes, direct dyes, surface active agents, oil agents, wetting agents, stabilizers, conditioning agents, silicone, hair protecting agents, thickening agents, pH adjusters, penetrants, hair tonic, ultraviolet light absorbers, coloring matters, pearl agents, antiseptic agents and perfumes.

Other oxidation dyes are not specifically restricted provided that they are dyes other than the aforesaid oxidation dye components (A) to (D). Examples of the dye intermediates include phenylenediamines other than the component (A), aminophenols other than the component (D), diaminopyridines, and their salts. Examples of the salts include hydrochlorides, sulfates and acetates. Of these, N,N-bis(2-hydroxyethyl)-p-phenylenediamine, 2-(2'-hydroxyethyl)-p-phenylenediamine, N-phenyl-p-phenylenediamine, 4,4'-diaminodiphenylamine, 2-chloro-p-phenylenediamine, N,N-dimethyl-p-phenylenediamine, o-aminophenol, p-methylaminophenol, 2,6-dichloro-p-phenylenediamine, p-aminophenylsufamic acid, 2,5-diaminopyridine, and their salts can be particularly added.

As the couplers, pyrogallol, catechol, m-aminophenol, m-phenylenediamine, 2,4-diaminophenol, 1,2,4-benzenetriol, toluene-3,4-diamine, toluene-2,4-diamine, hydroquinone, 2,6-diaminopyridine, 3,3'-iminodiphenol, 1,5-dihydroxynaphthalene, p-amino-o-cresol, diphenylamine, fluoroglucine, 2,4-diaminophenoxyethanol, gallic acid, tannic acid, ethyl gallate, methyl gallate, propyl gallate, Japanese gall(gobaishi), 1-methoxy-2-amino-4-(2-hydroxyethyl)aminobenzene, 5-(2-hydroxyethylamino)-2-methylphenol, their salts, etc. can be added. In addition, oxidation dyes described in "The Japanese Standards of Quasi-drugs Ingredients" (issued in June 1991, Yakuji Nippo, Ltd.) can be properly employed.

As the direct dyes, those publicly known, such as tar-based dyes and natural dyes, are employable. In particular, there can be mentioned nitro dye, azo dye, nitroso dye, triphenylmethane dye, xanthene dye, quinoline dye, anthraquinone dye and indigo dye. Examples of such dyes include nitro-p-phenylenediamine, p-nitor-o-phenylenediamine, p-nitro-m-phenylenediamine, 2-amino-4-nitrophenol, 2-amino-5-nitrophenol, picramic acid, N1,N4,N4-tris(2-hydroxyethyl)-2-nitroparaphenylenediamine (HC Blue #2), 4-[(2-nitrophenyl)amino]phenol (HC Orange #1), N1-(2-hydroxyethyl)-2-nitroparaphenylenediamine (HC Red #3), 2,2'-[(4-amino-3-nitrophenyl)imino]bisethanol (HC Red #13), N-(2-hydroxyethyl)-2-nitroaniline (HC Yellow #2), 2-[(2-(2-hydroxyethoxy)-4-nitrophenyl)amino]ethanol (HC Yellow #4), N1-(2-hydroxyethyl)-4-nitroorthophenylenediamine (HC Yellow w#5), their salts, and acid dyes regulated by "Ordinances to Regulate Tar Dyes Employable for Drugs, etc." (notified in 1966, the Ministry of Public Welfare), such as Red No. 2, Red No. 3, Red No. 102, Red No. 104-(1), Red No. 105-(1), Red No. 106, Red No. 201, Red No. 227, Red No. 230-(1), Red No. 230-(2), Red No. 231, Red No. 232, Red No. 401, Red No. 502, Red No. 503, Red No. 504, Red No. 506, Yellow No. 4, Yellow No. 5, Yellow No. 202-(1), Yellow No. 202-(2), Yellow No. 203, Yellow No. 402, Yellow No. 403-(1), Yellow No. 406, Yellow No. 407, Orange No. 205, Orange No. 207, Orange No. 402, Green No. 3, Green No. 204, Green No. F205, Green No. 401, Green No. 402, Brown No. 201, Purple No. 401, Blue No. 1, Blue No. 2, Blue No. 202, Blue No. 203, Blue No. 205 and Black No. 401.

As the surface active agent, any of a nonionic surface active agent, an anionic surface active agent, a cationic surface active agent and an amphoteric surface active agent may be employed.

Examples of the nonionic surface active agents include:

polyoxyethylene alkyl ethers, such as polyoxyethylene isostearyl ether, polyoxyethylene isocetyl ether, polyoxyethylene oleyl ether, polyoxyethylene oleylcetyl ether, polyoxyethylene stearyl ether, polyoxyethylene cetyl ether, polyoxyethylene cetostearyl ether, polyoxyethylene butyl ether, polyoxyethylene behenyl ether, polyoxyethylene myristyl ether, polyoxyethylene lauryl ether, polyoxyethylene tridecyl ether, polyoxyethylene hexyldecyl ether, polyoxyethylene octyldodecyl ether, polyoxyethylene decylpentadecyl ether and polyoxyethylene decyltetradecyl ether;

polyoxy alkylphenyl ethers, such as polyoxyethylene octylphenyl ether, polyoxyethylene dinonylphenyl ether and polyoxyethylene nonylphenyl ether;

polyoxyethylene polyoxypropylene alkyl ethers, such as polyoxyethylene polyoxypropylene stearyl ether, polyoxyethylene polyoxypropylene cetyl ether, polyoxyethylene polyoxypropylene decyltetradecyl ether, polyoxyethylene polyoxypropylene butyl ether and polyoxyethylene polyoxypropylene lauryl ether;

polyhydric alcohol fatty acid esters, such as propylene glycol monostearate;

glycerol fatty acid esters, such as glyceryl monomyristate, and polyglycerol fatty acid esters, such as decaglyceryl monolaurate;

sorbitan fatty acid esters, such as sorbitan monopalmitate;

polyoxyethylene glycerol fatty acid esters, such as polyoxyethylene glyceryl monostearate;

polyoxyethylene sorbitan fatty acid esters, such as polyoxyethylene sorbitan trioleate;

polyoxyethylene sorbitol fatty acid esters, such as polyoxyethylene sorbitol tetraoleate;

polyethylene glycol fatty acid esters, such as polyethylene glycol monostarate;

alkyl alkanol amides, such as coconut fatty acid diethanolamide;

polyoxyethylene hardened castor oil, polyoxythylene lanolin, polyoxyethylene cholesterol, polyoxyethylene phytosterol, polyoxyethylene cholestanol, and polyoxyethylene phytostanol.

Examples of the anionic surface active agents include:

alkyl sulfates, such as sodium lauryl sulfate, triethanolamine lauryl sulfate, ammonium lauryl sulfate, sodium cetyl sulfate, sodium stearyl sulfate and potassium lauryl sulfate;

polyoxyethylene alkyl/alkylallyl ether sulfates, such as sodium polyoxyethylene (abbreviated to POE hereinafter) lauryl ether sulfate, triethanolamine POE lauryl ether sulfate, ammonium POE lauryl ether sulfate, sodium POE alkyl ether sulfate, triethanolamine POE alkyl ether sulfate, ammonium POE alkyl ether sulfate and sodium POE nonylphenyl ether sulfate;

sulfosuccinates, such as sodium sulfosuccinate, disodium lauryl sulfosuccinate, disodium POE sulfosuccinate, disodium POE lauryl sulfosuccinate, disodium lauroyl ethanolamide POE sulfosuccinate and disodium undecylenoylamidoethyl sulfosuccinate;

N-acyl sulfonates, such as sodium cocoylmethyl taurate and sodium lauroylmethyl taurate;

alkylbenzenesulfnates, such as triethanolamine dodecylbenzenesulfonate;

α-olefinsulfonates, such as sodium tetradecenesulfonate;

N-acrylamino acid salts, such as sodium lauroyl sarcosinate, sodium N-lauroyl-L-glutamate, disodium N-stearoyl-L-glutamate and sodium N-myristoyl-L-glutamate; and POE alkyl ether phosphoric acids and their salts, such as POE lauryl ether phosphoric acid.

Examples of the cationic surface active agents include:

quaternary ammonium salts, such as stearyl trimethyl ammonium salts, cetyl trimethyl ammonium salts, alkyl trimethyl ammonium salts and distearyl dimethyl ammonium salts;

fatty acid amide amine salts, alkyl trialkylene glycol ammonium salts, benzalkonium salts, benzethonium salts, pyridinium salts, and imidazolinium salts.

Examples of the amphoteric surface active agents include:

those of betaine type, such as lauryl dimethylaminoacetic acid betaine, cocamide propyl betaine, oleamide propyl betaine, lauramide propyl betaine, cocobetaine, oleyl betaine, lauryl betaine, cetyl betaine and sulfobetaine;

those of imdazoline type, such as sodium 2-undecyl-N,N,N-(hydroxyethylcarboxymethyl)-2-imidazoline, 2-cocoyl-2-imidazolinium hydroxide-1-carboxyethyloxydisodium salt and 2-heptadecyl-N-carboxymethyl-N-hydroxyethylimidazolinium betaine; and those of amino acid type, such as glycine type and aminopropionic acid type.

Examples of the Oil Agents Include:

hydrocarbons, such as paraffin, liquid paraffin, liquid isoparaffin, light liquid isoparaffin, vaseline, squalane, microcrystalline wax, ceresin and pristane;

oils and fats, such as olive oil, Tsubaki oil, tea seed oil, Sasanqua oil, safflower oil, sunflower seed oil, soybean oil, cottonseed oil, sesame oil, beef tallow, cacao butter, corn oil, peanut oil, rape seed oil, rice bran oil, rice germ oil, wheat germ oil, coix seed oil, grape seed oil, almond oil, avocado oil, carrot oil, macadamia nut oil, castor oil, linseed oil, coconut oil, mink oil and egg yolk oil;

waxes, such as beeswax, candelilla wax, carnauba wax, jojoba wax and lanolin;

higher alcohols, such as lauryl alcohol, myristyl alcohol, cetyl alcohol, cetostearyl alcohol, stearyl alcohol, behenyl alcohol, oleyl alcohol and isostearyl alcohol;

higher fatty acids, such as lauric acid, myristic acid, plamitic acid, stearic acid, behenic acid, oleic acid, hydroxystearic acid, undecylenic acid, tall oil fatty acid, isostearic acid, linoleic acid and linolenic acid; and esters, such as isopropyl myristate, cetyl octanoate, cetyl isooctanoate, octyldodecyl myristate, isopropyl palmitate, butyl stearate, stearyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate and lanolin derivatives.

Examples of the wetting agents include glycerol, propylene glycol, 1,3-butylene glycol and polyethylene glycol.

Examples of the stabilizers include sulfite, ascorbic acid, erythorbic acid, thioglycolate, cysteine, edetate, etidronate, phenacetin and salicylic acid.

Examples of the conditioning agents include cationized cellulose, cationized quar gum, cationized polymer, cationized resin and natural water-soluble high molecular compound.

Examples of the silicones include polysiloxane, methyl polysiloxane, dimethyl polysiloxane, methylphenyl polysiloxane, methyl cyclopolysiloxane, highly polymerized methyl polysiloxane, polyether modified silicone and amino modified silicone.

Examples of the hair protecting agents include protein, polypeptide and amino acid.

Examples of the thickening agents include carboxyethyl cellulose, xanthane gum, carboxyvinyl polymer, and ethylene/acrylic acid polymer.

Examples of the pH adjustors include phosphoric acid, citric acid and sodium citrate.

Hair Coloring Agent Set

The first hair coloring agent composition and the second hair coloring agent composition of the invention may be each used in the form of a hair coloring agent set comprising a first agent which is any one of the first and the second hair coloring agent compositions and a second agent containing an oxidizing agent such as hydrogen peroxide.

In case of such a set, the first agent and the second agent can be separately preserved when the set is not used, and when the set is used, the first agent and the second agent each of which has been previously prepared are mixed and the mixture is applied to hair, whereby the hair can be colored. Therefore, such a set has excellent long-term preservability and is convenient.

The second agent has only to be a composition preferably containing hydrogen peroxide and water and capable of allowing the oxidation dye component in the first agent to develop a color.

The materials to constitute the second agent are not specifically restricted, but specifically, there can be mentioned, for example, hydrogen peroxide water, water, surface active agent, oil and fat, wetting agent, pH adjustor and stabilizer. Examples of the water, the surface active agents, the oils and fats, the wetting agents and the stabilizers, which can be added to the second agent, include the same ones as previously exemplified for the first hair coloring agent composition and the second hair coloring agent composition of the invention.

Hydrogen peroxide can be used so that it should be contained in an amount of usually 0.35 to 6% by weight when the whole amount of the second agent is 100% by weight, and for example, hydrogen peroxide water having a concentration of 35% by weight can be used in an amount of 1 to 17% by weight.

The first agent and the second agent may be each in any form such as a liquid form, a cream form, an emulsion form or a gel form, but preferable is a cream form from the viewpoint that in the application of the agent to hair, dropping of the agent can be prevented and efficient application is feasible.

The hair coloring agent set is used by mixing the first agent with the second agent immediately before application to hair. In the use of the first agent and the second agent, it is desirable to mix them in a weight ratio (first agent:second agent) of usually 1:3 to 3:1, preferably 1:2 to 2:1, particularly preferably 1:1, though the mixing ratio is not specifically restricted.

The pH of an oxidation hair coloring agent composition obtained by mixing the first agent with the second agent is desired to be in the range of 4.0 to 11.0.

A hair coloring method using the hair coloring agent set is, for example, a usual hair coloring method comprising mixing the first agent with the second agent to prepare an oxidation hair coloring agent, then applying the oxidation hair coloring agent to hair and washing the hair after a lapse of a given period of time.

If hair to be colored has a virgin hair portion (uncolored hair portion) and an already-colored hair portion and if a color difference between the virgin hair portion (uncolored hair portion) and the already-colored hair portion is relatively small, these portions can be colored on the same level by applying the same oxidation hair coloring agent to the hair without separately coloring these portions with different oxidation hair coloring agents and then washing the hair. However, if a damage of the already-colored hair portion is not negligible, it is possible that two kinds of the second agents one of which has a decreased concentration of hydrogen peroxide are prepared, for example, a second agent which is used for the virgin hair portion (uncolored hair portion) and has a hydrogen peroxide concentration of 6% by weight and a second agent which is used for the already-colored hair portion and has a hydrogen peroxide concentration of 3% by weight are prepared, then each of these second agents and the first agent are mixed to prepare two kinds of oxidation hair coloring agents, and they are separately applied to the corresponding portions.

EXAMPLES

The present invention is further described with reference to the following examples, but it should be construed that the invention is in no way limited to those examples.

Example A1

Preparation of First Hair Coloring Agent Composition (First Agent) of the Invention In a reaction vessel equipped with a stirring device, cetanol, liquid paraffin, polyoxythylene stearyl ether, stearyl trimethyl ammonium chloride and polyethylene glycol were placed, and they were heated to 85° C. to give a solution. With stirring, to the solution was slowly added a solution obtained by dissolving p-phenylenediamine, α-naphthol, resorcin, p-amino-o-cresol and sodium sulfite in purified water at 85° C. With further stirring, the resulting solution was cooled down to 30° C., and then, 28 wt % aqueous ammonia was added to obtain a creamy first agent. The amounts (% by weight) of the components used are set forth in Table 1.

Preparation of Second Agent

Using materials shown in Table 2 in amounts shown in Table 2, a creamy second agent having a hydrogen peroxide content of 6% by weight was prepared in a conventional manner.

Hair Coloring and Evaluation (1) Hair Coloring Operation

The first agent and the second agent prepared above were mixed in a weight ratio of 1:1 (first agent:second agent) to prepare an oxidation hair coloring agent. This oxidation hair coloring agent was applied to commercially available bleached hair (level 17, available from Beaulax Co., Ltd.). The hair was allowed to stand for 30 minutes at room temperature, then washed with a commercially available shampoo, rinsed with a commercially available treatment agent, then washed with water and dried. The resulting hair bunch was regarded as a hair bunch "immediately after coloring".

A color (L*a*b* color space) of the hair bunch "immediately after coloring" was measured by a color difference meter (CR-200, manufactured by Minolta Camera Co., Ltd.). A mean value of the measured values obtained by measurements of 9 times is set forth in Table 1 as the evaluation result.

(2) Evaluation of Degree of Color Fading

Operations consisting of washing the hair bunch "immediately after coloring" obtained in the above (1) with a commercially available shampoo, rinsing it with a commercially available treatment agent, washing it with water and drying it were repeated 7 times, and the resulting hair bunch was regarded as a hair bunch "after color fading". The hair bunch "immediately after coloring" and the hair bunch "after color fading" were visually observed by 10 panelists to examine a difference in color between those bunches, and the difference was evaluated based on the following evaluation criteria. A mean value of the values obtained by evaluation by the panelists was regarded as the evaluation result. The result is set forth in Table 1.

Evaluation Criteria (5-Rank Evaluation)

5 points: There is little difference in color between "immediately after coloring" and "after color fading".

4 points: There is a small difference in color between "immediately after coloring" and "after color fading".

3 points: There is a moderate difference in color between "immediately after coloring" and "after color fading".

2 points: There is a large difference in color between "immediately after coloring" and "after color fading".

1 point: There is an extremely large difference in color between "immediately after coloring" and "after color fading".

(3) Evaluation of Degree of Discoloration

Operations consisting of washing the hair bunch "immediately after coloring" obtained in the above (1) with a commercially available shampoo, rinsing it with a commercially available treatment agent, washing it with water and drying it were repeated 7 times, and the resulting hair bunch was regarded as a hair bunch "after discoloration". The hair bunch "immediately after coloring" and the hair bunch "after discoloration" were visually observed by 10 panelists to examine a difference in hue between those bunches, and the difference was evaluated based on the following evaluation criteria. A mean value of the values obtained by evaluation by the panelists was regarded as the evaluation result. The result is set forth in Table 1.

Evaluation Criteria (5-Rank Evaluation)

5 points: There is little difference in hue between "immediately after coloring" and "after discoloration".

4 points: There is a small difference in hue between "immediately after coloring" and "after discoloration".

3 points: There is a moderate difference in hue between "immediately after coloring" and "after discoloration".

2 points: There is a large difference in hue between "immediately after coloring" and "after discoloration".

1 point: There is an extremely large difference in hue between "immediately after coloring" and "after discoloration".

Examples A2 to A11

First agents were each prepared in the same manner as in Example A1, except that the components used and the amounts (% by weight) thereof in the preparation of the first agent were changed as shown in Table 1.

Using the resulting first agents and a second agent prepared in the same manner as in Example A1, hair coloring was carried out in the same manner as in Example A1, and then evaluation was carried out in the same manner as in Example A1.

The results are set forth in Table 1.

Examples B1 to B12

Preparation of Second Hair Coloring Agent Composition (First Agent) of the Invention First agents, that is, the second hair coloring agent compositions of the invention, were each prepared in the same manner as in Example A1, except that the components used and the amounts (% by weight) thereof in the preparation of the first agent were changed as shown in Table 3.

Preparation of Second Agent

A second agent was prepared in the same manner as in Example A1.

Hair Coloring and Evaluation

Using the resulting first agents and the resulting second agent, hair coloring was carried out in the same manner as in Example A1, and then evaluation was carried out in the same manner as in Example A1. The results are set forth in Table 3.

Comparative Examples 1 to 13

First agents were each prepared in the same manner as in Example A1, except that the components used and the amounts (% by weight) thereof in the preparation of the first agent were changed as shown in Table 4.

Using the resulting first agents and a second agent prepared in the same manner as in Example A1, hair coloring was carried out in the same manner as in Example A1, and then evaluation was carried out in the same manner as in Example A1.

The results are set forth in Table 4.

TABLE 1

| | | (unit: % by weight) | First agent | | | | | | | | | | |
|---|---|---|---|---|---|---|---|---|---|---|---|---|---|
| | | | Ex. A1 | Ex. A2 | Ex. A3 | Ex. A4 | Ex. A5 | Ex. A6 | Ex. A7 | Ex. A8 | Ex. A9 | Ex. A10 | Ex. A11 |
| Dye component | (A) | (a1) p-Phenylenediamine | 0.40 | 0.40 | 0.40 | 0.40 | 0.40 | 0.40 | 0.40 | 0.33 | 0.07 | 0.26 | 0.14 |
| | | (a2) Toluene-2,5-diamine | — | — | — | — | — | — | — | 0.07 | 0.33 | 0.14 | 0.26 |
| | (B) | α-Naphthol | 0.13 | 0.13 | 0.05 | 0.35 | 0.12 | 0.13 | 0.27 | 0.13 | 0.13 | 0.13 | 0.13 |
| | (C) | Resorcin | 0.27 | 0.27 | 0.19 | 0.55 | 0.19 | 0.22 | 0.45 | 0.27 | 0.27 | 0.27 | 0.27 |
| | (D) | p-Aminophenol | — | — | — | — | — | — | — | — | — | — | — |
| | | p-Amino-o-cresol | 0.07 | — | 0.40 | — | 0.06 | — | — | — | 0.07 | — | 0.07 |
| | | m-Aminophenol | — | 0.07 | — | 0.40 | — | 0.06 | — | 0.07 | — | 0.07 | — |
| Others | | Cetanol | 4 | 4 | 4 | 4 | 4 | 4 | 4 | 4 | 4 | 4 | 4 |
| | | Liquid paraffin | 8 | 8 | 8 | 8 | 8 | 8 | 8 | 8 | 8 | 8 | 8 |
| | | Polyoxyethylene stearyl ether | 5 | 5 | 5 | 5 | 5 | 5 | 5 | 5 | 5 | 5 | 5 |
| | | Stearyl trimethyl ammonium chloride | 1 | 1 | 1 | 1 | 1 | 1 | 1 | 1 | 1 | 1 | 1 |
| | | Polyethylene glycol | 5 | 5 | 5 | 5 | 5 | 5 | 5 | 5 | 5 | 5 | 5 |
| | | Sodium sulfite | 0.6 | 0.6 | 0.6 | 0.6 | 0.6 | 0.6 | 0.6 | 0.6 | 0.6 | 0.6 | 0.6 |
| | | 28 wt % Aqueous ammonia | 7 | 7 | 7 | 7 | 7 | 7 | 7 | 7 | 7 | 7 | 7 |
| | | Purified water | Make up to 100 | | | | | | | | | | |
| | | (A) + (B) + (C)/dye components (% by weight) | 91.95 | 91.95 | 61.54 | 76.47 | 92.21 | 92.59 | 100.00 | 91.95 | 91.95 | 91.95 | 91.95 |

TABLE 1-continued

| (unit: % by weight) | | First agent | | | | | | | | | | |
|---|---|---|---|---|---|---|---|---|---|---|---|---|
| | | Ex. A1 | Ex. A2 | Ex. A3 | Ex. A4 | Ex. A5 | Ex. A6 | Ex. A7 | Ex. A8 | Ex. A9 | Ex. A10 | Ex. A11 |
| Weight ratio | (A) | 1 | 1 | 1 | 1 | 1 | 1 | 1 | 1 | 1 | 1 | 1 |
| | (B) | 0.33 | 0.33 | 0.13 | 0.88 | 0.30 | 0.33 | 0.68 | 0.33 | 0.33 | 0.33 | 0.33 |
| | (C) | 0.68 | 0.68 | 0.48 | 1.38 | 0.48 | 0.55 | 1.13 | 0.68 | 0.68 | 0.68 | 0.68 |
| (a1)/(a2) molar ratio | | — | — | — | — | — | — | — | 5.33 | 0.24 | 2.10 | 0.61 |
| Color immediately after coloring | $L^*$ | 25.03 | 23.25 | 20.64 | 19.48 | 25.03 | 23.25 | 28.22 | 24.52 | 29.84 | 25.18 | 29.04 |
| | $a^*$ | 7.48 | 4.45 | 10.2 | 5.83 | 8.11 | 4.45 | 5.08 | 4.54 | 7.62 | 4.61 | 7.56 |
| | $b^*$ | 5.81 | 4.54 | 2.33 | −1.15 | 5.81 | 4.54 | 6.02 | 4.66 | 6.08 | 4.72 | 5.99 |
| Degree of color fading | | 4.4 | 4.5 | 3.7 | 4.0 | 3.9 | 4.2 | 4.4 | 4.5 | 4.5 | 4.6 | 4.8 |
| Degree of discoloration | | 4.4 | 4.3 | 3.9 | 3.6 | 4.0 | 4.0 | 4.4 | 4.4 | 4.5 | 4.5 | 4.7 |

TABLE 2

| (unit: % by weight) | Second agent |
|---|---|
| Cetanol | 2.0 |
| Liquid paraffin | 4.0 |
| Polyoxyethylene stearyl ether | 5.0 |
| Stearyl trimethyl ammonium chloride | 1.0 |
| Polyethylene glycol | 5.0 |
| 35 wt % Hydrogen peroxide water | 16.0 |
| 85 wt % Phosphoric acid | 0.1 |
| Phenacetin | 0.1 |
| Purified water | Make up to 100 |

TABLE 3

| (unit: % by weight) | | | First agent | | | | | | | | | | | |
|---|---|---|---|---|---|---|---|---|---|---|---|---|---|---|
| | | | Ex. B1 | Ex. B2 | Ex. B3 | Ex. B4 | Ex. B5 | Ex. B6 | Ex. B7 | Ex. B8 | Ex. B9 | Ex. B10 | Ex. B11 | Ex. B12 |
| Dye component | (A) | (a1) p-Phenylenediamine | 0.40 | 0.40 | 0.40 | 0.40 | 0.40 | 0.40 | 0.40 | 0.40 | 0.33 | 0.07 | 0.26 | 0.14 |
| | | (a2) Toluene-2,5-diamine | — | — | — | — | — | — | — | — | 0.07 | 0.33 | 0.14 | 0.26 |
| | (B) | α-Naphthol | 0.13 | 0.13 | 0.05 | 0.35 | 0.11 | 0.35 | 0.12 | 0.27 | 0.13 | 0.13 | 0.13 | 0.13 |
| | (C) | Resorcin | 0.27 | 0.27 | 0.19 | 0.55 | 0.19 | 0.55 | 0.22 | 0.45 | 0.27 | 0.27 | 0.27 | 0.27 |
| | (D) | p-Aminophenol | 0.27 | 0.27 | 0.03 | 0.79 | 0.05 | 0.58 | 0.10 | 0.38 | 0.27 | 0.27 | 0.27 | 0.27 |
| | | p-Amino-o-cresol | 0.07 | — | 0.35 | 0.65 | — | — | 0.06 | — | 0.07 | — | 0.07 | — |
| | | m-Aminophenol | — | 0.07 | — | — | 0.06 | 0.06 | — | — | — | 0.07 | — | 0.07 |
| Others | | Cetanol | 4 | 4 | 4 | 4 | 4 | 4 | 4 | 4 | 4 | 4 | 4 | 4 |
| | | Liquid paraffin | 8 | 8 | 8 | 8 | 48 | 8 | 8 | 8 | 8 | 8 | 8 | 8 |
| | | Polyoxyethylene stearyl ether | 5 | 5 | 5 | 5 | 5 | 5 | 5 | 5 | 5 | 5 | 5 | 5 |
| | | Stearyl trimethyl ammonium chloride | 1 | 1 | 1 | 1 | 1 | 1 | 1 | 1 | 1 | 1 | 1 | 1 |
| | | Polyethylene glycol | 5 | 5 | 5 | 5 | 50 | 5 | 5 | 5 | 5 | 5 | 5 | 5 |
| | | Sodium sulfite | 0.6 | 0.6 | 0.6 | 0.6 | 0.6 | 0.6 | 0.6 | 0.6 | 0.6 | 0.6 | 0.6 | 0.6 |
| | | 28 wt % Aqueous ammonia | 7 | 7 | 7 | 7 | 7 | 7 | 7 | 7 | 7 | 7 | 7 | 7 |
| | | Purified water | | | | | | Make up to 100 | | | | | | |
| (A) + (B) + (C) + (D)/dye components (% by weight) | | | 93.86 | 93.86 | 65.69 | 76.28 | 92.59 | 96.91 | 93.33 | 100 | 93.86 | 93.86 | 93.86 | 93.86 |
| Weight ratio | (A) | | 1 | 1 | 1 | 1 | 1 | 1 | 1 | 1 | 1 | 1 | 1 | 1 |
| | (B) | | 0.33 | 0.33 | 0.13 | 0.88 | 0.28 | 0.88 | 0.30 | 0.68 | 0.33 | 0.33 | 0.33 | 0.33 |
| | (C) | | 0.68 | 0.68 | 0.48 | 1.38 | 0.48 | 1.38 | 0.55 | 1.13 | 0.68 | 0.68 | 0.68 | 0.68 |
| | (D) | | 0.68 | 0.68 | 0.08 | 1.98 | 0.13 | 1.45 | 0.25 | 0.95 | 0.68 | 0.68 | 0.68 | 0.68 |
| (a1)/(a2) molar ratio | | | — | — | — | — | — | — | — | — | 5.33 | 0.24 | 2.10 | 0.61 |
| Color immediately after coloring | $L^*$ | | 27.12 | 26.45 | 22.58 | 23.51 | 22.97 | 24.33 | 26.28 | 23.54 | 27.55 | 27.47 | 27.10 | 27.25 |
| | $a^*$ | | 7.92 | 7.40 | 10.2 | 13.71 | 7.28 | 7.10 | 6.22 | 6.51 | 8.21 | 7.75 | 8.26 | 7.60 |
| | $b^*$ | | 9.94 | 8.27 | 3.41 | 5.12 | 3.15 | 5.83 | 7.28 | 3.61 | 10.05 | 8.48 | 10.15 | 8.41 |
| Degree of color fading | | | 4.7 | 4.8 | 4.1 | 4.1 | 4.2 | 4.4 | 4.4 | 4.7 | 4.8 | 4.8 | 4.8 | 4.8 |
| Degree of discoloration | | | 4.8 | 4.7 | 4.5 | 4.8 | 4.5 | 4.4 | 4.7 | 4.7 | 4.8 | 4.8 | 4.9 | 4.8 |

TABLE 4

| (unit: % by weight) | | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|---|---|---|---|---|---|---|---|
| | | | | | | | | First agent | | | | | | | |
| Dye component | (A) | (a1) p-Phenylenediamine | 0.40 | 0.40 | 0.40 | 0.40 | 0.40 | 0.40 | 0.40 | 0.40 | 0.40 | 0.40 | 0.40 | 0.40 | 0.40 |
| | | (a2) Toluene-2,5-diamine | — | — | — | — | — | — | — | — | — | 0.07 | 0.33 | 0.14 | 0.26 |
| | (B) | α-Naphthol | 0.13 | 0.13 | 0.13 | 0.13 | 0.50 | 0.03 | 0.13 | 0.13 | 0.50 | 0.03 | 0.13 | 0.13 | 0.13 |
| | (C) | Resorcin | 0.27 | 0.27 | 0.27 | 0.27 | 0.27 | 0.27 | 0.65 | 0.16 | 0.27 | 0.27 | 0.65 | 0.16 | 0.27 |
| | (D) | p-Aminophenol | — | — | 0.27 | 0.27 | — | — | — | — | 0.27 | 0.27 | 0.27 | 0.27 | 0.88 |
| | | p-Amino-o-cresol | 1.33 | — | 1.33 | — | — | 0.07 | — | 0.07 | 0.07 | — | — | 0.07 | — |
| | | m-Aminophenol | — | 1.33 | — | 1.33 | 0.07 | — | 0.07 | — | — | 0.07 | 0.07 | — | 0.07 |
| Others | | Cetanol | 4 | 4 | 4 | 4 | 4 | 4 | 4 | 4 | 4 | 4 | 4 | 4 | 4 |
| | | Liquid paraffin | 8 | 8 | 8 | 8 | 8 | 8 | 8 | 8 | 8 | 8 | 8 | 8 | 8 |
| | | Polyoxyethylene stearyl ether | 5 | 5 | 5 | 5 | 5 | 5 | 5 | 5 | 5 | 5 | 5 | 5 | 5 |
| | | Stearyl trimethyl ammonium chloride | 1 | 1 | 1 | 1 | 1 | 1 | 1 | 1 | 1 | 1 | 1 | 1 | 1 |
| | | Polyethylene glycol | 5 | 5 | 5 | 5 | 5 | 5 | 5 | 5 | 5 | 5 | 5 | 5 | 5 |
| | | Sodium sulfite | 0.6 | 0.6 | 0.6 | 0.6 | 0.6 | 0.6 | 0.6 | 0.6 | 0.6 | 0.6 | 0.6 | 0.6 | 0.6 |
| | | 28 wt % Aqueous ammonia | 7 | 7 | 7 | 7 | 7 | 7 | 7 | 7 | 7 | 7 | 7 | 7 | 7 |
| | | Purified water | | | | | | Make up to 100 | | | | | | | |
| (A) + (B) + (C) + (D)/dye components (% by weight) | | | 37.56 | 37.56 | — | — | 94.35 | 90.91 | 94.40 | 90.79 | — | — | — | — | — |
| (A) + (B) + (C) + (D)/dye components (% by weight) | | | — | — | 44.58 | 44.58 | — | — | — | — | 95.36 | 93.27 | 95.39 | 93.20 | 96.00 |
| Weight ratio | (A) | | 1 | 1 | 1 | 1 | 1 | 1 | 1 | 1 | 1 | 1 | 1 | 1 | 1 |
| | (B) | | 0.33 | 0.33 | 0.33 | 0.33 | 0.25 | 1.08 | 0.33 | 0.33 | 1.25 | 0.08 | 0.33 | 0.33 | 0.33 |
| | (C) | | 0.68 | 0.68 | 0.68 | 0.68 | 0.68 | 0.68 | 1.63 | 0.40 | 0.68 | 0.68 | 1.63 | 0.40 | 0.68 |
| | (D) | | — | — | 0.68 | 0.68 | — | — | — | — | 0.68 | 0.68 | 0.68 | 0.68 | 2.20 |
| Color immediately after coloring | L* | | 22.45 | 21.46 | 22.44 | 23.44 | 21.42 | 22.82 | 22.90 | 23.12 | 22.48 | 26.89 | 25.15 | 27.25 | 29.98 |
| | a* | | 16.05 | 7.74 | 15.76 | 8.96 | 6.64 | 5.89 | 4.12 | 7.27 | 8.83 | 5.55 | 6.31 | 9.01 | 8.73 |
| | b* | | 1.52 | 1.15 | 5.10 | 3.86 | 0.22 | 7.27 | 5.49 | 3.54 | 3.06 | 8.68 | 7.30 | 7.65 | 15.81 |
| Degree of color fading | | | 1.3 | 1.6 | 2.1 | 2.2 | 3.1 | 2.0 | 2.4 | 2.0 | 2.4 | 3.2 | 3.2 | 2.7 | 1.7 |
| Degree of discoloration | | | 2.8 | 1.3 | 2.7 | 1.8 | 2.2 | 2.9 | 3.0 | 1.8 | 2.6 | 2.4 | 1.8 | 2.2 | 3.3 |

It can be seen from Table 1, Table 3 and Table 4 that in the Example A group and the Example B group, color fading and discoloration of hair after hair washing were both inhibited more effectively as compared with the comparative examples. Further, it can be seen that color fading and discoloration of hair were more inhibited in the Example B group than in the Example A group, and particularly, discoloration was conspicuously inhibited.

As described hereinbefore, the hair coloring agent composition of the invention is preferable for coloring hair and is useful in the industry of manufacturing hair coloring agent compositions and in the barber and beauty parlors business.

The invention claimed is:

1. A hair coloring agent composition comprising (A) one or more compounds selected from the group consisting of p-phenylenediamine, toluene-2,5-diamine and their salts, (B) α-naphthol and (C) resorcin (with the proviso that p-aminophenol is not contained), wherein:

the components (A), (B) and (C) are contained in a total amount of 60 to 100% by weight when the total amount of dye components in the hair coloring agent composition is 100% by weight, and based on 1 part by weight of the component (A), the component (B) is contained in an amount of 0.1 to 1 part by weight, and the component (C) is contained in an amount of 0.45 to 1.5 parts by weight.

2. The hair coloring agent composition as claimed in claim 1, wherein at least p-phenylenediamine and/or its salt is contained as the component (A).

3. The hair coloring agent composition as claimed in claim 2, wherein p-phenylenediamine and/or its salt and toluene-2,5-diamine and/or its salt are contained as the component (A)

in a molar ratio (p-phenylenediamine and/or its salt:toluene-2,5-diamine and/or its salt) of 0.226:1 to 5.65:1.

4. The hair coloring agent composition as claimed in claim 1, wherein the components (A), (B) and (C) are contained in a total amount of 0.1 to 5.0% by weight in the whole amount of the hair coloring agent composition.

5. A hair coloring agent composition comprising (A) one or more compounds selected from the group consisting of p-phenylenediamine, toluene-2,5-diamine and their salts, (B) α-naphthol, (C) resorcin and (D) p-aminophenol, wherein:
the components (A), (B), (C) and (D) are contained in a total amount of 60 to 100% by weight when the total amount of dye components in the hair coloring agent composition is 100% by weight, and
based on 1 part by weight of the component (A), the component (B) is contained in an amount of 0.1 to 1 part by weight, the component (C) is contained in an amount of 0.45 to 1.5 parts by weight, and the component (D) is contained in an amount of 0.05 to 2 parts by weight.

6. The hair coloring agent composition as claimed in claim 5, wherein at least p-phenylenediamine and/or its salt is contained as the component (A).

7. The hair coloring agent composition as claimed in claim 6, wherein p-phenylenediamine and/or its salt and toluene-2,5-diamine and/or its salt are contained as the component (A) in a molar ratio (p-phenylenediamine and/or its salt:toluene-2,5-diamine and/or its salt) of 0.226:1 to 5.65:1.

8. The hair coloring agent composition as claimed in claim 5, wherein the components (A), (B), (C) and (D) are contained in a total amount of 0.1 to 5.0% by weight in the whole amount of the hair coloring agent composition.

9. The hair coloring agent composition as claimed in claim 6, wherein the components (A), (B), (C) and (D) are contained in a total amount of 0.1 to 5.0% by weight in the whole amount of the hair coloring agent composition.

10. The hair coloring agent composition as claimed in claim 7, wherein the components (A), (B), (C) and (D) are contained in a total amount of 0.1 to 5.0% by weight in the whole amount of the hair coloring agent composition.

11. The hair coloring agent composition as claimed in claim 2, wherein the components (A), (B) and (C) are contained in a total amount of 0.1 to 5.0% by weight in the whole amount of the hair coloring agent composition.

12. The hair coloring agent composition as claimed in claim 3, wherein the components (A), (B) and (C) are contained in a total amount of 0.1 to 5.0% by weight in the whole amount of the hair coloring agent composition.

* * * * *